United States Patent [19]

Knight et al.

[11] 4,443,541

[45] Apr. 17, 1984

[54] PROCESS FOR PREPARING AN INDENEDIONE AND A MYCOBACTERIUM CULTURE THEREFOR

[75] Inventors: John C. Knight; Merle G. Wovcha, both of Kalamazoo, Mich.

[73] Assignee: The Upjohn Company, Kalamazoo, Mich.

[21] Appl. No.: 384,831

[22] Filed: Jun. 4, 1982

Related U.S. Application Data

[63] Continuation-in-part of Ser. No. 375,914, May 7, 1982, abandoned.

[51] Int. Cl.$^3$ .......................... C12P 7/38; C12P 33/16; C12N 1/20; C12R 1/33

[52] U.S. Cl. ...................................... 435/149; 435/55; 435/253; 435/865

[58] Field of Search .................. 435/149, 55, 253, 865

[56] References Cited

U.S. PATENT DOCUMENTS 4,042,459  8/1977  Knight et al. ....................... 435/125

*Primary Examiner*—Alvin E. Tanenholtz
*Attorney, Agent, or Firm*—Sidney B. Williams, Jr.; William G. Jameson

[57] ABSTRACT

A process for the microbiological conversion of steroids to (2+)-(7aS) 2,3,7,7-tetrahydro-7a-methyl-(1H)-indene-1,5(6H)-dione, hereinafter referred to as the indenedione.

5 Claims, No Drawings

PROCESS FOR PREPARING AN INDENEDIONE AND A MYCOBACTERIUM CULTURE THEREFOR

This application is a continuation-in-part of application Ser. No. 375,914 filed May 7, 1982 and now abandoned.

BACKGROUND OF THE INVENTION

The transformation of steroids by microorganisms has been widely studied and documented. Apparently, the earliest such work was by Mamoli and Vercellone in 1937, Ber. 70, 470 and Ber. 70, 2079. They disclosed the reduction of 7-ketosteroids to 17β-hydroxysteroids by fermenting yeast. Since then, Peterson and Murray disclosed the 11α-hydroxylation of progesterone with the fungus *Rhizopus nigricans;* see U.S. Pat. No. 2,602,769 (1952). Kraychy et al. in U.S. Pat. No. 3,684,657 (1972) discloses the selective microbiological degradation of steroidal 17-alkyls by fermenting a steroid containing at least 8 carbons in the 17-alkyl side chain with Myobacterium sp. NRRL B-3683 to prepare androst-4-ene-3,17-dione (AD), androst-1,4-diene-3,27-dione (ADD), and 20α-hydroxymethylpregna-1,4-dien-3-one. Marsheck et al. in U.S. Pat. No. 3,759,791 (1973) disclose the selective microbiological preparation of androst-4-ene-3,27-dione by fermenting a steroid of the cholestane or stigmastane series containing at least 8 carbons in the 17-alkyl side chain with Mycobacterium sp. NRRL B-3805.

U.S. Pat. No. 4,029,549 discloses a process for preparing 9α-hydroxy-3-ketobisnorchol-4-en-22-oic using the microorganism *Mycobacterium fortuitum,* NRRL B-8119.

U.S. Pat. No. 4,293,646 discloses a process for preparing predominantly AD using the microorganism *Mycobacterium fortuitum,* NRRL B-11359.

BRIEF SUMMARY OF THE INVENTION

The subject process is an improved process for preparing the indenedione having the formula I. The compound formed by the process of this invention is known, and is useful as an intermediate in the chemical synthesis of useful steroids. It has been chemically synthesized by, among others, Boyce and Whitehurst, J. Chem. Soc. 2022 (1959), Hajos et al., Tetrahedron, 24, 2039 (1968), and Micheli et al., J. Org. Chem. 40: 675–681 (1975). Also, U.S. Pat. Nos. 3,714,262, 3,897,460, 3,907,827 and Velluz et al., Angewandte Chemi 4: 181 (1965) disclose methods of using the indenedione. However, to our knowledge this compound has never been previously isolated as an intermediate in the microbial degradation of steroids. The mutant of the subject process, *Mycobacterium fortuitum,* NRRL B-15026, is a mutant of *Mycobacterium fortuitum* ATCC 6842.

*M. fortuitum* NRRL B-15026 is characterized by its ability to selectively transform steroids with or without 17-hydrocarbon side chains, and accumulate the indenedione as the principal transformed product in the fermentation beer.

The mutant can be obtained by using the mutation procedures disclosed herein or other mutation procedures. The mutant of the subject invention is obtained by growing *M. fortuitum* ATCC 6842, which is then subjected to nitrosoguanidine (NTG) mutagensis.

The selection and isolation of the mutant can be accomplished by procedures disclosed herein or by other mutation procedures. Such a procedure is detailed in U.S. Pat. No. 4,293,646.

*Mycobacterium fortuitum* NRRL B-15026 is used to selectively transform steroids with or without 17-hydrocarbon side chains to indenedione I. As used herein the term hydrocarbon means those saturated and unsaturated hydrocarbon groups that are known by those skilled in the art as substituents at the 17-position. Examples of suitable steroid substrates are sitosterols, cholesterol, stigmasterol, campesterol, and like steroids. These steroid substrates can be in either the pure or crude form.

The process of this invention is especially useful because it results directly in the production of optically active indenedione I. Alternative processes, for example, those described by Micheli et al. and Hajos et al., involve multi-step asymmetric synthesis or optical resolution of a racemate.

DETAILED DESCRIPTION OF THE INVENTION

The Microorganisms

Mutants which are characterized by their ability to selectively degrade steroids in the fermentation beer can be obtained by mutating microorganisms of the following genera: Athrobacter, Bacillus, Brevibacterium, Corynebacterium, Microbacterium, Micobacterium, Nocardia, Protaminobacter, Serratia, and Streptomyces. *Mycobacterium fortuitum* ATCC 6842 has been mutated, as disclosed herein, to give a novel laboratory mutant microorganism. The 1974 ATCC Catalogue discloses the following alongside the listing of ATCC 6842: "J. C. Cruz 2, Cold Abscess. Acta Med. Rio de Janeiro 1:1 (1936). Medium 90 37C". *M. fortuitum* ATCC 6842 degrades sterols non-selectively to small molecular weight compounds, e.g. $CO_2 + H_2O$. Thus, this microorganism is not suitable as a selective steroid degrader.

Mutation of *M. fortuitum* ATCC 6842 using nitrosoguanidine has resulted in the production of a mutant which selectively degrades steroids with or without 17-hydrocarbon side chains to produce (2+)-(7aS)-2,3,7,7a-tetrahydro-7a-methyl-(1H)-indene-1,5-(6H)-dione. This mutant microorganism of *M. fortuitum* has been given the accession number NRRL B-15026 by the Northern Regional Research Laboratory, U.S. Department of Agriculture, Peoria, Ill., U.S.A., where it has been deposited in the permanent collection. A subculture of this microorganism is freely available from this depository by request made thereto. it should be understood that the availability of the culture does not constitute a license to practice the subject invention in derogation of patent rights granted with the subject instrument by governmental action.

The morphology and drug sensitivities of *M. fortuitum* NRRL B-15026 are indistinguishable from that of the parent *M. fortuitum,* ATCC 6842. Both *M. fortuitum* cultures are acid-fast non-motile, non-sporeforming bacilli belonging to the family Mycobacteriaceae of the order Actinomycetales. According to Runyon's classification, Runyon, E. H. 1959 Med. Clin. North America 43:273, it is a nonchromogenic group IV mycobacterium, i.e., it grows rapidly at low temperature to produce nonpigmented colonies on relatively simple media.

*M. fortuitum* ATCC 6842 and *M. fortuitum* NRRL B-15026 are clearly distinguishable in their action on steroid molecules. As disclosed above, *M. fortuitum* ATCC 6842 is a non-selective degrader of steroids, whereas *M. fortuitum* NRRL B-15026 is a selective degrader. This property of *M. fortuitum* NRRL B-15026 makes it highly useful, as disclosed herein.

The mutation of *M. fortuitum* ATCC 6842 to give *M. fortuitum* NRRL B-15026 was accomplished by the use of nitrosoguanidine. The details of the procedure are described infra. Though mutation procedures are generally known in the art, there is no known art which teaches or even suggests the type of mutants, if any, which might be obtained by use of the subject mutation procedure. Also, though the mutation and transformation procedures, disclosed herein, are detailed for a mycobacterium, it should be understood that similar or equivalent procedures can be used with microorganisms of the other genera, as disclosed herein.

The Transformation Process

The selective transformation of the subject invention can be effected in a growing culture of *M. fortuitum* NRRL B-15026 by either adding the selected steroid substrate to the culture during the incubation period, or incorporating it in the nutrient medium prior to inoculation. The steroid can be added singly or in combination with another steroid. The preferred, but not limiting, range of concentration of the steroid in the culture is about 0.1 to about 100 grams per liter. The culture is grown in a nutrient medium containing a carbon source, for example, an assimilable carbohydrate, and a nitrogen source, for example, an assimilable nitrogen compound or proteinaceous material. Preferred carbon sources include glucose, brown sugar, sucrose, glycerol, starch, cornstarch, lactose, dextrin, molasses, and the like. Preferred nitrogen sources include cornsteep liquor, yeast, autolyzed brewer's yeast with milk solids, soybean meal, cottonseed meal, cornmeal, milk solids, pancreatic digest of casein, fish meal, distillers' solids, animal peptone liquors, meat and bone scraps, ammonium salts and the like. Combinations of these carbon and nitrogen sources can be used advantageously. Trace metals, for example, zinc, magnesium, manganese, cobalt, iron, and the like, need not be added to the fermentation media since tap water and unpurified ingredients are used as components of the medium prior to sterilization of the medium.

The transformation process can range from about 72 hours to 15 days or more. The incubation temperature can range from about 25° C. to about 37° C., with 32° C. being preferred for NRRL B-15026. The contents are aerated with sterilized air and agitated to facilitate growth of the microorganism and, thus, enhance the effectiveness of the transformation process.

Upon completion of the transformation process, as evidenced by thin layer chromatography (tlc) using silica gel plates (E. Merck, Darmstadt) and a solvent system consisting of 2:3 (by volume) ethylacetate:cyclohexane, the desired transformed steroid is recovered by means well known in the art. For example, the fermentation (transformation) reaction mixture, including the fermentation liquor and cells, can be extracted with a water-immiscible organic solvent for steroids. Suitable solvents include dichloromethane (preferred), methylene chloride, chloroform, ethylene chloride, trichloroethylene, ether, amyl acetate and the like.

Alternatively, the fermentation liquor and cells can be first separated by conventional methods, e.g., filtration or centrifugation, and then separately extracted with suitable solvents. The cells can be extracted with either water-miscible or water-immiscible solvents. The fermentation liquor, freed of cells, can be extracted with water-immiscible solvents.

The extracts can be filtered through diatomaceous earth and the filtrate vacuum distilled to dryness. The resulting residue containing the desired transformed steroid then can be dissolved in a minimum of ethyl acetate:cyclohexane (20:80). This solution then can be chromatographed on silica gel. Indenedione I can be separated from the silica gel by elution with the solvent system ethyl acetate-chloroform (15:85). The compound then can be isolated as a separate entity by evaporation of the solvent and recrystallization from hexane.

The desired product of the subject invention transformation process is the known steroid intermediate indenedione I.

EXAMPLE 1

Preparation of mutant *M. fortuitum* NRRL B-15026 from *M. fortuitum* ATCC 6842 a. Nitrosoguanidine Mutagenesis

Cells of *M. fortuitum* ATCC 6842 are grown at 28° C. in the following sterile seed medium:

| | |
|---|---|
| TWEEN 80 | 1 g/liter |
| Nutrient Broth (Difco) | 8 g/liter |
| Yeast Extract | 1 g/liter |
| Glycerol | 5 g/liter |
| Distilled Water, q.s. | 1 liter |

The pH is adjusted to 7.0 prior to sterilization at 121° C. for 20 minutes.

The cells are grown to a density of about $5 \times 10$ per ml, pelleted by centrifugation, and then washed with an equal volume of sterile 0.1 M sodium citrate, pH 5.6 containing 0.1% TWEEN 80. Washed cells are resuspended in the same volume of citrate buffer, a sample removed for titering (cell count), and nitrosoguanidine added to a final concentration of 50 $\mu$g/ml. The cell suspension is incubated at 37° C. in a water bath for 30 minutes, after which a sample is again removed for titering and the remainder centrifuged down and washed with an equal volume of sterile 0.1 M potassium phosphate, pH 7.0. Finally, the cells are resuspended in a sterile 0.9% saline solution containing 0.1% TWEEN 80. The cells are then plated out to select for mutants.

b. Selection And Isolation of Mutant *M. fortuitum* NRRL B-15026

Mutagenized cells, as described above, are diluted and spread onto plates containing a medium consisting of the following:

| | |
|---|---|
| Glycerol | 10.0 g/liter |
| K$_2$HPO$_4$ | 0.25 g/liter |
| NH$_4$NO$_3$ | 1.0 g/liter |
| MgSO$_4$.7H$_2$O | 0.25 g/liter |
| FeSO$_4$.7H$_2$O | 0.001 g/liter |
| Distilled Water, q.s. | 1 liter |

The pH is adjusted to 7.0, agar (15 g/liter) is added, and the medium is autoclaved at 121° C. for 30 minutes and then poured into sterile Petri plates.

Growth on this medium eliminates most nutritional auxotrophs produced by the mutagensis procedure, e.g., cultures that require vitamins, growth factors, etc. in order to grow on chemically defined medium are eliminated. After incubation at 32° C. for about 7 days, the resulting colonies are replicated to test plates suitable for selecting mutants and then back onto control plates containing the glycerol-based medium. The test plates are prepared as described by Peterson, G. E., H. L. Lewis and J. R. Davis. 1962. "Preparation of Uniform Dispersions of Cholesterol and Other Water-Insoluble Carbon Sources in Agar Media." J. Lipid Research 3:275–276. The minimal salts medium in these plates is described above in section (b) of Example 1. An appropriate carbon source (1.0 g/liter), such as AD is added in place of glycerol and the resulting suspension autoclaved for 30 minutes at 121° C. The sterile, hot mixture is then poured into a sterile blender vessel, blended for several minutes, and then poured into sterile Petri plates. Foaming tends to be a problem in this procedure but can be reduced by blending when the mixture is hot and by flaming the surface of hot molten agar plates. In this manner uniform dispersions of water-insoluble carbon sources are obtained which facilitates the preparation of very homogenous but opaque agar plates.

Colonies which grew well on the control plates, but very slowly, if at all, on test plates containing AD as the sole carbon course, are purified by streaking onto nutrient agar plates. After growth at 32° C., individual clones are picked from the nutrient agar plates with sterile toothpicks and retested by inoculating gridded plates containing AD as the carbon source. Purified isolates which still exhibit a phenotype different from the parental culture are then evaluated in shake flasks.

c. Shake Flask Evaluation

Shake Flasks (500 ml) contain 100 ml of biotransformation medium consisting of the following ingredients:

| Glucose | 5.0 g/liter |
| --- | --- |
| $K_2HPO_4$ | 0.5 g/liter |
| $NH_4Cl$ | 3.0 g/liter |
| $MgSO_4.7H_2O$ | 2.0 g/liter |
| $CaCO_3$ | 3.0 g/liter |
| $Na_3C_6H_5O_7.2H_2O$ | 3.0 g/liter |
| Urea | 0.5 g/liter |
| TWEEN 80 | 2.0 g/liter |
| Ucon | 8.0 g/liter |
| Tap Water, q.s. | 1 liter |

The pH is adjusted to 7.0.

Soyflour (1 g/liter) is blended into the medium and then sitosterol (30 g/liter) is also blended into the medium. After the flasks are autoclaved for 20 minutes at 121° C., they are cooled to 32° C. and then inoculated with 10 ml of seed growth prepared as follows:

The purified isolates from part (b) are grown on agar slants at 32° C. A loop of cells taken from a slant is used to inoculate a 500-ml flask containing 100 ml of sterile seed medium consisting of the following ingredients:

| TWEEN 80 | 1 g/liter |
| --- | --- |
| Nutrient Broth (Difco) | 8 g/liter |
| Yeast Extract | 1 g/liter |
| Glycerol | 5 g/liter |
| Distilled Water, q.s. | 1 liter |

The pH is adjusted to 7.0 prior to autoclaving the flasks at 121° C. for 20 minutes. The seed flasks are incubated at 32° C. for 72 hours.

As disclosed above, 10 ml of seed growth is then used to inoculate each 500-ml flask containing 100 ml of sterile transformation medium. The flasks are then incubated at 32° C. on a rotary shaker and sampled at various intervals. Ten ml samples are removed and extracted by shaking with 3 volumes of methylene chloride. Portions of the extracts are analyzed by thin layer chromatography using silica gel and the solvent system described above, i.e., 2:3 (by volume) ethyl acetate:cyclohexane, and by gas-liquid chromatography. Evidence of the presence of (2+)-(7aS)-2,3,7,7a-tetrahydro-7α-methyl-(1H)-indene-1,5-(6H)-dione confirms the selective degradation of sitosterol by the mutant produced from the parent M. fortuitum ATCC 6842.

EXAMPLE 2

Transformation of Sitosterol to (2+)-(7aS)-2,3,7,7a-tetrahydro-7a-methyl-(1H)-indene-1,5-(6H)-dione (a) Fermentation of crude sitosterol The biotransformation medium is the same as described in Example 1(c). This medium is inoculated with 10 parts of a seed culture of the mutant M. fortitutum NRRL-B-15026 prepared as described in Example 1(c). The inoculated mixture is incubated at 32° C. for 336 hours with agitation to promote submerged growth. Following incubation, the mixture is extracted with methylene chloride and the product isolated as detailed in section (b) below.

(b) Isolation of the Product

The crude methylene chloride extract of the fermentation beer is concentrated to a brown oil (10.85 g), and subjected to a preliminary chromatographic separation on a short silica column to separate the products from antifoam and highly polar materials. The column is eluted in succession with the following solvents (200 ml each): (1) hexane:toluene 1:1; (2) toluene; (3) methylene chloride; (4) ethyl acetate; and (5) ethyl acetate:methanol 4:1. Fractions 2 and 3 (combined weight 3.9 g) contained a uv-absorbing component with the same Rf value on tlc as a synthetic sample of the indenedione (tlc system ethyl acetate:hexane 1:1). The combined fractions are rechromatographed on three prepacked silica columns in series (Lobar, size B; E. Merck) in the system methylene chloride:methanol 97:3. Appropriate fractions are repooled on the basis of tlc, and rechromatographed in ethyl acetate/hexane 1:1. The indenedione is isolated as a pale yellow oil, which after treatment with activated carbon crystallized from ethyl acetate/methylene chloride as long colorless needles (200 mg) mp 65°–66°, $(\alpha)+412°$ ($CHCl_3$). [Reported values (3) mp 66°–66.5°, $(\alpha)+362°$ in benzene]. The structure is confirmed by mass spectrometry (Mol. ion m/e 164, spectrum the same as a synthetic sample) and nmr: $^{13}C$-nmr 20.6, (7a-methyl); 216.4, (1-keto); 198, (5-keto); 169.7, (C-3a); 123.9δ, (C-4). H-nmr, 1.3, (7a-methyl); 5.98δ, (4-H).

EXAMPLE 3

By substituting cholesterol, stigmasterol, or campesterol for sitosterol in the fermentation, as described in Example 2, there is produced (2+)-(7aS)-2,3,7,7a-tetrahydro-7a-methyl-(1H)-indene-1,5-(6H)-dione.

CHART A

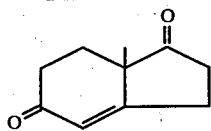

Formula I

We claim:

1. A process for preparing (2+)-(7aS)-2,3,7,7a-tetrahydro-7a-methyl-(1H)-indene-1,5(6H)-dione which comprises cultivating *Mycobacterium fortuitum* NRRL B-15026 in a fermentation beer, in an aqueous, nutrient medium under aerobic conditions in the presence of a steroid with or without 17-hydrocarbon side chains to produce (2+)-(7aS)-2,3,7,7a-tetrahydro-7a-methyl-(1H)-indene-1,5(6H)-dione in the fermentation beer and isolating (2+)-(7aS)-2,3,7,7a-tetrahydro-7a-methyl-(1H)-indene-1,5(6H)-dione from the fermentation beer.

2. A process according to claim 1 wherein said microorganism is cultivated in an aqueous nutrient medium under aerobic conditions in the presence of a steroid with or without a 17-hydrocarbon side chain.

3. A process according to claim 1 wherein said steroid is selected from the group consisting of cholesterol, sitosterol, stigmasterol and campesterol.

4. A process for preparing (2+)-(7aS)-2,3,7,7a-tetrahydro-7a-methyl-(1H)-indene-1,5-(6H)-dione which comprises (a) cultivating *Mycobacterium fortuitum* NRRL B-15026 in an aqueous nutrient medium under aerobic conditions in the presence of a steroid with or without 17-hydrocarbon side chains to produce (2+)-(7aS)-2,3,7,7a-tetrahydro-7a-methyl-(1H)-indene-1,5-(6H)-dione in a fermentation beer; (b) extracting a mixture from the beer with methylene chloride; (c) concentrating the mixture to give an oil; (d) subjecting the oil to chromatography; (e) treating (2+)-(7aS)-2,3,7,7a-tetrahydro-7a-methyl-(1H)-indene 1,5-(6H)-dione obtained by chromatography with activated carbon; (f) crystallization of (2+)-(7aS)-2,3,7,7a-tetrahydro-7a-methyl (1H)-indene-1,5-(6H)-dione from a solvent.

5. A biologically pure culture of mutant of *Mycobacterium fortuitum*, having the deposit accession number NRRL B-15026, which is characterized by its ability to selectively degrade steroids with or without 17-hydrocarbon side chains, in the presence of an aqueous nutrient medium and aerobic conditions, and to accumulate (2+)-(7aS)-2,3,7,7a-tetrahydro-7a-methyl-(1H)-indene-1,5(6H)-dione in the fermentation beer.

* * * * *